United States Patent [19]

Hiltunen

[11] Patent Number: 5,125,842

[45] Date of Patent: Jun. 30, 1992

[54] METHOD OF MONITORING THE CURING OF DENTAL RESINS

[76] Inventor: Neil S. Hiltunen, 2 Juniper Rd., North Hampton, N.H. 03862-0820

[21] Appl. No.: 679,282

[22] Filed: Apr. 2, 1991

[51] Int. Cl.⁵ ............................................. A61C 5/04
[52] U.S. Cl. .................................................... 433/226
[58] Field of Search .................. 433/226, 25, 26, 72; 249/170, 173

[56] References Cited

U.S. PATENT DOCUMENTS

| | | | |
|---|---|---|---|
| 333,191 | 12/1885 | Anderson | 249/170 |
| 1,040,314 | 10/1912 | Harding | 249/170 |
| 1,857,289 | 5/1932 | Schwartz | 249/54 |
| 3,295,208 | 11/1962 | Redtenbacher | 433/72 |
| 3,815,851 | 7/1974 | Girard | 249/121 |
| 4,505,675 | 3/1985 | Albert | 433/72 |
| 4,969,811 | 11/1990 | Littleton | 425/116 |

OTHER PUBLICATIONS

Resin Depth of Cure Test, Clinical Research Associates Newsletter, vol. 15, Issue 11, Nov. 1991.
Regular Testing of Curing Lights helps Reduce Restoration Failure, Dental Products Report, Dec. 1991.

*Primary Examiner*—Gene Mancene
*Assistant Examiner*—Andy A. Cherichetti
*Attorney, Agent, or Firm*—Foley & Lardner

[57] ABSTRACT

A method and apparatus for checking the depth of cure of resins used to fill restorative cavities in teeth employs an opaque calibration box having two sections which can be placed adjacent each other to form, in the top of the apparatus, a plurality of holes of varying depths. A sample of a resin to be used in filling the restorative cavity is placed into a hole having a depth approximately the same as the depth of the restorative cavity in the tooth. The sample is then exposed to the curing light which will be used to cure the resin in the restorative cavity of the tooth. The sections of the calibration box are separated to determine the depth of cure at various points in time. The time required to cure the resin in the opaque calibration box determines the time required to cure the resin when it is inserted into a restorative cavity of approximately the same depth in the tooth. Periodic monitoring of curing characteristics using the calibration box also allows evaluation of the efficacy of a curing light over time.

6 Claims, 1 Drawing Sheet

METHOD OF MONITORING THE CURING OF DENTAL RESINS

BACKGROUND OF THE INVENTION

1. Field of the Invention

The invention relates to light curing of resins used to fill teeth and bond porcelain veneers and fillings to teeth. In particular, the method and apparatus of the invention relate to determining the curing characteristics of such resins.

2. Related Art

The state of the art in dental materials involves the use of light cured resins to fill teeth and to bond porcelain veneers and fillings to teeth. Curing these materials requires the use of a high intensity light that causes the resin to harden. Curing times are in the range of 20 or more seconds, depending on the thickness and translucency of the resin and the intensity of the light. These factors are not easily measurable or always constant. The intensity of curing lights can vary from manufacturer to manufacturer and may not be constant over time. For example, the light may deteriorate over time, depending on the bulb, internal light filter and fiber optics.

Depth of cure is important information for a dentist to know. The depth of cure determines how long a light needs to be held over a restoration to assure complete hardening to the bottom where it bonds to the tooth. Since this can vary from 20 seconds to more than a minute, a dentist cannot be certain at any point and time if the material has completely cured. Removal of the curing light prior to complete curing of the resin invites failure of the restoration. On the other hand, excessively long curing is an inefficient use of time which ultimately results in higher cost to patients. In addition, it is not possible for a dentist to determine if the efficiency or effectiveness of a curing light is diminishing over time. Thus, the dentist could be unaware that a previously adequate curing duration may have become inadequate as a result of diminishing efficacy of the curing light. This further reduces the chances of clinical success of a filling or bonding.

To date, there has been no convenient means of determining depth of cure of resins used in dental restorations. Due to the importance of this information for effective dental restorations it is desirable to have an apparatus for checking resin cure characteristics before the resin is used to fill a restoration cavity. U.S. Pat. No. 3,295,208 to Redtenbacher discloses an apparatus for determining the working length of root canal instruments. While Redtenbacher discloses the use of a box in the dental field to establish the working length of a particular instrument, it does not disclose of use such a box for calibrating the depth of cure of a resin.

U.S. Pat. No. 4,505,675 to Albert discloses a method and device for preparing an endodontic filler. While Albert '675 discloses the use a calibrated cavity for preparing material for filling a tooth, it to fails to disclose the use a hinged box for determining the cure of a resin to be used in filling a tooth.

U.S. Pat. No. 1,857,289 to Schwartz discloses an arrangement for making dental molds. However, there is no disclosure of checking the curing of a resin using calibrated cavities.

Finally, U.S. Pat. No. 3,815,851 to Girard discloses a mold for casting test samples but also fails to disclose use of a plurality of calibrated cavities to reveal the depth of cure.

SUMMARY AND OBJECTS OF THE INVENTION

In view of the above limitations in the state of the art, it is an object of the invention to provide a method and apparatus for determining required exposure time to a curing light to assure clinical success of a dental restoration.

It is a further object of the invention to provide a method and apparatus for calibrating the curing time required for resins in restorative cavities of different depths;

It is still another object of the invention to provide a method and apparatus for determining efficient curing times for dental resins used in restorative applications;

It is still another object of the invention to provide a simple and easily transportable curing check apparatus;

It is still another object of the invention to provide a method and apparatus for comparing the curing times of a plurality of dental resins at the same depth;

It is still another object of the invention to provide an apparatus which allows a dentist to visually inspect the curing of the dental resin at any time.

The above objects of the invention, and others, are accomplished by a resin cure monitoring apparatus which has two sections. Each of the two sections has one or more hole portions of predetermined depth. The sections can be joined together so that corresponding depth hole portions form sample holes. Dental resin is inserted into the sample holes and then exposed to the curing light. At any point in time, the dentist can separate the sections and inspect the resin to determine if sufficient time has elapsed to harden the resin to the desired depth. A plurality of holes of various depths is used to facilitate the calibration. In addition, a plurality of holes at each depth is provided to facilitate comparing the cure times of different resins at the same depth.

BRIEF DESCRIPTION OF THE DRAWINGS

The invention is described below with particular reference to the drawings in which.

DETAILED DESCRIPTION OF THE PREFERRED EMBODIMENTS

A dental resin cure checking apparatus according to the invention has first and second sections with hole portions or slots of predetermined depths. A first section has at least one such slot or hole portion typically with a corresponding slot or hole portion in the other section. The interior faces of each section can be positioned next to each other so that typically, the corresponding hole sections form a complete hole. It is also possible to arrange slots in either section with corresponding solid portions in the other section. A joining member holds the sections together when the faces are placed adjacent to each other. Resin to be cured is then inserted into the slots or holes and exposed to a curing light. Since the slots or holes are at a plurality of depths, the curing time for resins in the shallow holes will be less than the curing time for resins in the deeper holes. At any time, the two sections can be separated so that the resin can be inspected for depth of hardening or curing. The time to achieve complete curing for each depth with a particular curing light can then be recorded and used to determine the length of curing time required for dental fillings used in cavities of approximately the same depth in tooth restorative applications.

Figure 2:
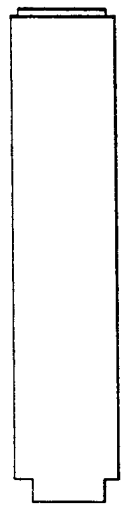
FIG. 2 is a closed side view of a cure checking apparatus according to the invention.
Figure 1:
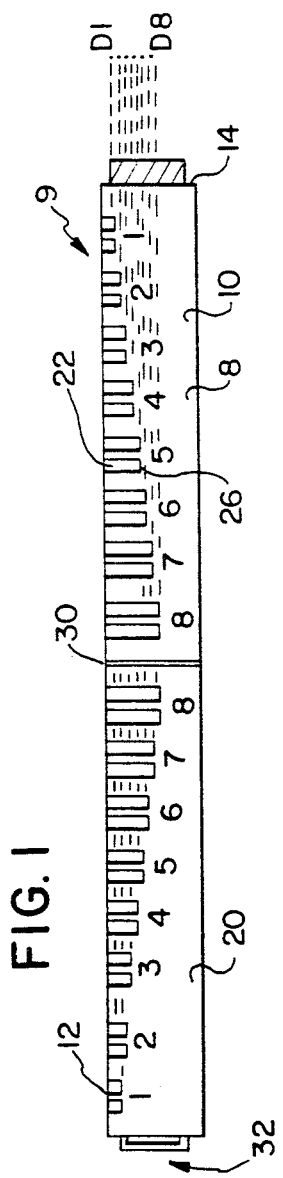
FIG. 1 is an open side view of a cure checking apparatus according to the invention.
Figure 3:
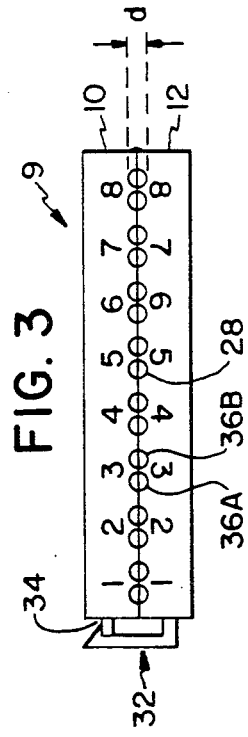
FIG. 3 is a closed top view of a cure checking apparatus according to the invention.
Figure 4:
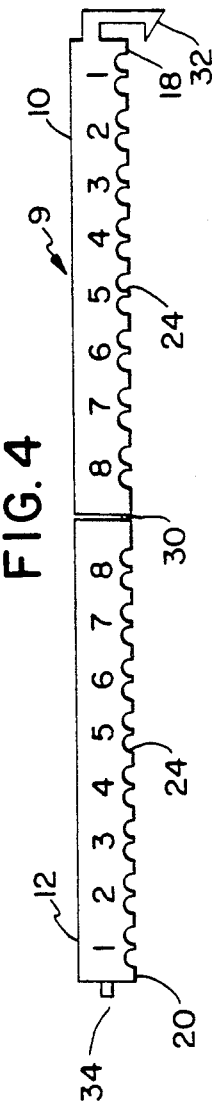
FIG. 4 is an open top view of a cure checking apparatus according to the invention.

FIG. 1 shows cure checking apparatus 9 with two sections 10 and 12. Each section has a plurality of hole portions 1-8. Typically, the depth of each hole portion $D1 \geq D8$ varies from 1-8 millimeters in 1 millimeter increments. However, any units of measure can be used and there is no limitation on the number and arrangement of hole portions. The holes also need not differ in depth from each other by the same increment. By way of illustration, and not limitation, the figures show an arrangement of holes of monotonically increasing depth from outside edges 14, 16 toward the other edge of each section 10, 12. However, if convenient, any number of hole portions can be arranged in any desired sequence. Each of the sections has a face 18, 20 which can be placed adjacent to each other as shown in FIG. 3. Slots or hole portions, e.g. 22, have an open upper section 24 and a solid bottom 26. As FIG. 4 illustrates, each hole portion 24 is open on the face portions 18, 20 of the sections 10, 12. When the face portions 18–20 are placed adjacent each other as shown in FIG. 3, holes 28 are formed. As the figures illustrate, the slots or hole portions in section 10 and 12 are arranged in the same order so that corresponding hole portions can be matched up to form the holes 28. When the faces of sections 10 and 12 are placed adjacent to each other, the holes 28 are formed to have a diameter, d, which is typically two millimeters. FIGS. 1-4 show the hole portions to be rounded. This by way of illustration, and not limitation, as it would be known to those of ordinary skill that other shapes of holes can be employed. It would also be known that any diameter, d, can be selected, appropriate to the application. It will also be known that the diameter of any slot in one section can be selected so that an open slot having a size approximately equal to a hole of diameter, d, can be formed in one section while the corresponding face is solid at the same position.

The figures further show hinge 30 as a joining member between the sections to facilitate locating faces 18 and 20 of sections 10 and 12 adjacent to each other. Hook 32 and clasp 34 serve as further joining members to hold sections 10 and 12 together in the closed position. It will be known to those of ordinary skill that such an arrangement is by way of illustration and not limitation. For example, the sections need not be hinged but could be separate and connectable using a dowel and hole arrangement. In addition, the dowel and hole arrangement could be keyed to prevent misalignment. Further, such a dowel and hole arrangement could incorporate a side screw as a positive closure mechanism. Other closure mechanisms could also be employed. These include bayonet connectors, hooks and engagement eyes, C-clamps, and other arrangements as would be known to those of ordinary skill to mate the individual sections.

In use, faces 18 and 20 of hole sections 10 and 12 are placed adjacent each other to form holes 28 as shown in FIG. 3. A filling resin is then inserted into one or more of the holes and exposed to a curing light. At any point in time, the sections 10 and 12 can be separated and the depth of cure of the resin in any particular hole inspected. The time required to achieve curing of the resin at particular depths in the calibration apparatus indicates the length of time for curing the resin with the same curing light when the resin is inserted into a restorative cavity of a tooth.

FIGS. 1-4 also show that more than one hole can be formed at each depth location. This facilitates comparing the amount of time required to cure different resins to the same depth. For example, a first resin could inserted in hole 36A and a second resin in hole 36B, which are formed at depth location 3 when faces 18 and 20 of sections 10 and 12 are placed adjacent each other. As previously discussed, the curing characteristics of each resin can be determined by separating the sections 10 and 12 after exposing the resins to a curing light for a period of time. By inserting different resins in holes 36A and 36B, and periodically examining the curing, the hardening characteristics of the two resins at the same depth can be compared. Of course, any number of holes can be formed at any number of depths to facilitate such comparisions.

The invention provides the further advantage that the cure checking or calibration box can be formed in a relatively small and light weight size. For example, the sections of the box could be formed of a material which does not adhere to the resin, such as polyethylene. Thus, the cure checking or calibration box can be easily transported within an office or to other locations where various curing lights can be tested and evaluated. In addition, by periodically testing the time required to achieve resin curing to various depths, the performance of a curing light can be recorded and monitored. The invention has the further advantage that curing to a plurality of depths can be monitored. Therefore, the existence of non-linearities in the rate of curing to different depths or other variations in curing characteristics of resins can be identified.

While several embodiments of the invention have been described, it will be understood that it is capable of further modifications, and this application is intended to cover any variations, uses, or adaptations of the invention, following in general the principles of the invention and including such departures from the present disclosure as to come within knowledge or customary practice in the art to which the invention pertains, and as may be applied to the essential features hereinbefore set forth and falling within the scope of the invention or the limits of the appended claims.

What is claimed is:

1. A method of curing a filling in a dental restoration, the method comprising the steps of:
   inserting filling material into a restoration cavity of a known depth;
   thereafter, exposing the filling to a curing light for a time approximately the same as a curing time determined to cure a sample of the filling material in a curing calibration apparatus having a hole with a depth approximately the same as the known depth of the restoration cavity.

2. The method recited in claim 1 wherein the curing time is predetermined by curing a sample of the filling material before inserting filling material into the restoration cavity.

3. The method recited in claim 1 wherein the curing time is determined contemporaneously with curing of the filling material in the restoration cavity.

4. The method recited in claim 1 wherein the step of curing a sample of the filling material in a calibration apparatus further comprises:
- joining together two sections of the calibration apparatus, each section having a portion of at least one hole with approximately a same depth as the known depth of the restoration cavity, thereby forming a sample hole of the known depth of the restoration cavity in the calibration apparatus;
- inserting the sample of filling material into the hole in the calibration apparatus;
- exposing the sample inserted in the hole to the curing light; and
- separating the sections of the calibration apparatus and inspecting the filling material to determine time required for curing.

5. The method recited in claim 4 wherein the sections of the calibration apparatus, when joined, form a plurality of holes of different depth, each depth approximately corresponding to a restoration cavity depth, the method further comprising inserting the sample of filling material into one of the holes having a depth approximately corresponding to the depth of the restoration cavity.

6. A method of checking the cure of a sample of filling material, the method comprising the steps of:
- joining together face portions of first and second sections of a calibration apparatus, at least one of the sections having at least one slot with an opening on the face portion thereof, each slot having a predetermined depth;
- inserting samples of filling material into selected slots;
- exposing the samples inserted in the slots to a curing light; and
- separating the sections of the calibration apparatus and inspecting the filling material to determine time required for curing.

* * * * *